United States Patent [19]

Crossley et al.

[11] Patent Number: 4,725,605
[45] Date of Patent: Feb. 16, 1988

[54] THIAZOLO- AND THIAZINO-BENZIMIDAZOLES, AND THEIR USE AS ANTI-ULCER/HYPERSECRETION AGENTS

[75] Inventors: Roger Crossley, Reading; Peter J. Meade, Maidenhead, both of England

[73] Assignee: John Wyeth & Brother Limited, Maidenhead, England

[21] Appl. No.: 866,180

[22] Filed: May 22, 1986

Related U.S. Application Data

[63] Continuation-in-part of Ser. No. 619,869, Jun. 12, 1984, abandoned.

[30] Foreign Application Priority Data

Dec. 31, 1983 [GB] United Kingdom ............. 8333231

[51] Int. Cl.⁴ ............... A61K 31/38; C07D 513/04; C07D 215/16; C07D 413/04
[52] U.S. Cl. ........................ 514/338; 514/237; 514/238; 514/227; 514/254; 514/366; 514/307; 514/309; 514/310; 514/311; 514/312; 514/313; 514/314; 514/318; 514/322; 514/316; 548/151; 544/121; 544/124; 544/128; 544/133; 544/360; 544/363; 544/368; 546/141; 546/142; 546/143; 546/144; 546/155; 546/156; 546/157; 546/153; 546/159; 546/167; 546/193; 546/194; 546/195; 546/199; 546/187; 546/209; 546/140; 546/256; 546/271
[58] Field of Search ............. 548/151; 544/126, 361, 544/121, 124, 128, 133, 360, 363, 368; 546/141, 142, 143, 144, 155, 156, 157, 153, 159, 167, 193, 194, 195, 199, 187, 209, 140, 256, 271; 514/338, 237, 238, 227, 254, 366, 307, 309, 310, 311, 312, 313, 314, 318, 322, 316

[56] References Cited

U.S. PATENT DOCUMENTS 4,214,089 7/1980 Fenichel et al. ............ 548/151

FOREIGN PATENT DOCUMENTS 5583710 1/1982 Japan ............ 548/151

OTHER PUBLICATIONS

Indian J. Exp. Biology, 1972, 10(1) pp. 37–40 (Eng).
J. Het. Chem. 1969, 6(6) 797–802 (Eng).
Chem. Abstracts, vol. 71, 1969; 22067v.
Chem. Abstracts, vol. 81, 1974; 151141v.
Chem. Abstracts, vol. 92, 1980; 41839y.

Primary Examiner—Alan L. Rotman
Assistant Examiner—J. Richter
Attorney, Agent, or Firm—George Tarnowski

[57] ABSTRACT

This invention relates to a method of treating ulcers or hypersecretion in a mammal which comprises administering a compound of formula

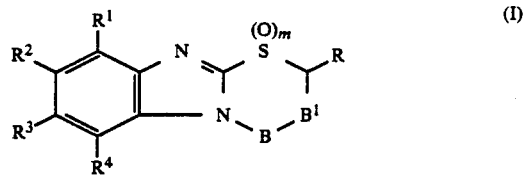

(I)

or a pharmaceutically acceptable salt thereof wherein —B—B¹— represents a chain of formula

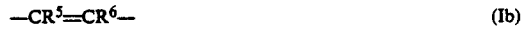

$-CR^5=CR^6-$ (Ib)

or

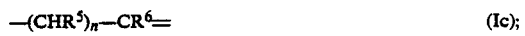

$-(CHR^5)_n-CR^6=$ (Ic);

R represents an optionally substituted aryl or heteroaryl radical; R¹, R², R³ and R⁴ independently represent hydrogen, or a defined substituent or any adjacent pair of R¹, R², R³ and R⁴ together with the carbon atoms to which they are attached complete a five or six membered saturated or unsaturated carbocyclic or heterocyclic ring, said ring being optionally substituted by a defined substituent said heterocyclic ring having at least one heteroatom selected from oxygen, nitrogen and sulphur. Novel compositions and compounds of formula I are also disclosed.

8 Claims, No Drawings

THIAZOLO- AND THIAZINO-BENZIMIDAZOLES, AND THEIR USE AS ANTI-ULCER/HYPERSECRETION AGENTS

This invention relates to a method for treating ulcers or hypersecretion with heterocyclic compounds more particularly benzimidazoles, to novel compositions comprising benzimidazoles and to the novel compounds themselves and their preparation and is a continuation-inpart of co-pending application Ser. No. 619,869 filed June 12, 1984 now abandoned.

2,3-Dihydrothiazino-benzimidazoles having hypotensive activity are disclosed in Japanese Kokai No. 8118989 (Chemical Abstracts 95: 80996d). Krasovskii OM in Farm. Zh (Kiev) 1979, (4) 33036 disclosed naphth-[1′, 2′:4,5]imidazo[2,1-b]-thiazoles in a study (no data) of compounds with antibacterial and antifungal activities. Thiazolo[3,2-a]benzimidazoles are described in the following Chemical Abstracts references: 72:43565s; 76:52165w; 81:151141v; 73:109740z; 71:22067v; 71:13065r; 76:153678w; 76:153679x and 92:41839y; but no pharmaceutical activity is ascribed to the compounds.

A series of thiazolo- and thiazino-benzimidazoles has been found which possesses pharmaceutical activity, in particular antiulcer activity and/or antisecretory activity and hence is useful in the treatment of ulcers or gastric hypersecretion. In particular the compounds are useful in the treatment of peptic ulcer disease. The compounds are also useful as intermediates to other compounds in the series.

Accordingly in one aspect this invention provides a method of treating ulcers or hypersecretion in a mammal which comprises administering to said mammal in need of such treatment an effective amount of a compound of formula:

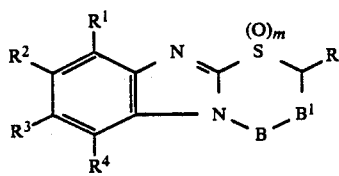
(I)

or a pharmaceutically acceptable salt thereof wherein —B—B$^1$— represents a chain of formula

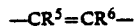 (Ib)

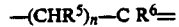 (Ic)

R represents an aryl or heteroaryl radical each optionally substituted by one or more substituents the same or different selected from lower alkylthio, lower alkyl, lower alkoxy, halogen, alkanoyloxy of 2 to 7 carbon atoms, lower alkoxycarbonyl, halolower alkyl, hydroxy, cyano, amino, mono- or diloweralkyl amino, lower alkanoylamino, carboxy, carboxyloweralkyl, hydroxyloweralkyl, carbamoyl, carbamoyloxy, lower alkyl- or aryl-carbonyl, (loweralkoxy)lower alkoxy, 1-piperidinyl, 4-morpholinyl, 4-loweralkylpiperazinyl, 1-pyrrolidinyl; OR$^8$, SR$^8$, phenyl and phenyl substituted by one or more substituents as hereinbefore defined excepting phenyl; (where R$^8$ is C$_2$–C$_6$ alkenyl, C$_3$–C$_{10}$ cycloalkyl, aryl, aralkyl or aryl or aralkyl each carrying from 1 to 3 substituents on the aryl selected from lower alkyl, halogen, nitro, haloloweralkyl, hydroxy and lower alkoxy).

R$^1$, R$^2$, R$^3$ and R$^4$ independently represent hydrogen, or a substituent as mentioned above in connection with the group R, or any adjacent pair of R$^1$, R$^2$, R$^3$ and R$^4$ together with the carbon atoms to which they are attached complete a five or six membered saturated or unsaturated carbocyclic or heterocyclic ring, said ring being optionally substituted by a substituent as defined above in connection with the group R, said heterocyclic ring having at least one heteroatom selected from oxygen, nitrogen and sulphur; R$^5$ and R$^6$ independently represent hydrogen or lower alkyl; n and m independently represent 0 or 1, the term "heteroaryl" means a monovalent aromatic heterocyclic group in which the ring heteroatom or atoms is/are selected from oxygen, nitrogen and sulphur; the term 'lower' means a group containing 1 to 6 carbon atoms.

In a second aspect this invention provides novel compounds of formula I as shown hereinabove or salts thereof, wherein R, R$^1$, R$^2$, R$^3$, R$^4$, m and —B—B$^1$— have the meanings given above with the provisos:

(i) when —B—B$^1$— is a chain of formula Ic, n is 0, R$^1$ and R$^2$ together with the carbon atoms to which they are attached represent a 6-membered unsaturated carbocyclic ring and R is phenyl, 2-thienyl, p-methoxyphenyl or p-bromophenyl then m is 1, or (ii) when —B—B$^1$ is a chain of formula Ic, n is 0, R$^6$ is hydrogen or lower alkyl and R$^1$, R$^2$ and R$^4$ are hydrogen, R$^3$ is hydrogen or hydroxy and R is phenyl, p-chlorophenyl, p-bromophenyl, p-tolyl, p-methoxyphenyl, p-phenylphenyl, 1-naphthyl or 2-thienyl, then m is 1.

In a third aspect this invention provides pharmaceutical compositions comprising a compound of formula I as shown hereinbefore or a pharmaceutically acceptable salt thereof.

Examples of any one of R$^{1-4}$ when substituents are methyl, ethyl, propyl, butyl, isopropyl, methoxy, ethoxy, propoxy, isopropoxy, butoxy, chlorine, bromine, fluorine, acetoxy, propionyloxy, butryloxy, methoxycarbonyl, ethoxycarbonyl, propoxycarbonyl, trifluoromethyl, hydroxy, cyano, amino, methylamino, dimethylamino, ethylamino, acetylamino, carboxy, carboxymethyl, hydroxymethyl, hydroxyethyl, carbamoyl, carbamoyloxy, acetyl, benzoyl or phenyl.

The group R is exemplified by (1) aryl radicals such as phenyl or naphthyl which can be substituted by one or more groups as listed above for any one of R$^{1-4}$, and (2) heteroaryl radicals especially those having one or more heteroatoms selected from oxygen, nitrogen and sulphur, such as pyridyl (e.g. pyrid-2-yl, pyrid-3-yl), thienyl (e.g. thien-2-yl) furyl (e.g. fur-2-yl), thiazolyl (e.g. thiazol-2-yl), or bicyclic groups such as quinolyl, isoquinolyl or indolyl, which groups can be substituted by one or more groups as listed above for any one of R$^{1-4}$. Examples of substituents for R also include (lower alkoxy)- lower alkoxy (e.g. methoxymethoxy, methoxy- and ethoxyethoxy), phenyl, halophenyl, loweralkylphenyl, loweralkoxyphenyl, methyl, methylthio, ethylthio, propylthio, butylthio, pentylthio, isopropylthio, t-butylthio, and groups of formula OR$^8$ or SR$^8$ where R$^8$ is vinyl; 1-propenyl; 3-butenyl; cyclopropyl; cyclobutyl; cyclopentyl; cyclohexyl; cycloheptyl; cyclooctyl; cyclononyl; cyclodecyl; 2-methylcyclopropyl; 2,2-dimethylcyclopropyl; 2-methylcyclobutyl; 2-methylcyclopentyl, 2-methylcyclohexyl; phenyl; o-, m- or p-tolyl; o-, m- or p-ethylphenyl; 2,3-, 3,4-, 3,5- or 2,5- dimethylphenyl; 2,3,5-, or 3,4,5-triethylphenyl; 2-,3- or 4-chlorophenyl; 2-,3- or 4-fluorophenyl; 2,3-, 3,4- or 2,4-dichlorophenyl; o-, m- or p- methoxyphenyl; 2,3-, 3,4-, or 2,4-dimethoxyphenyl; 2-chloro-3-methylphenyl; 2-chloro-4-methoxyphenyl; benzyl and 2-chlorobenzyl.

When any adjacent pair of $R^1$, $R^2$, $R^3$ and $R^4$ complete a fused ring examples of the additional rings are benzo and pyrido-fused rings. For example when $R^2$ and $R^3$ form a benzo fused ring the compound of formula I has the general formula

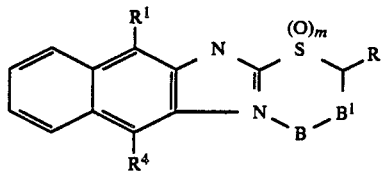

Examples of $R^5$ and $R^6$ when lower alkyl are methyl, ethyl, propyl.

In the compounds of formula I preferred value for —B—$B^1$- is formula Ic especially where n is 0.

Preferably R represents a phenyl or pyridyl group e.g. pyrid-2- or 3-yl which may be substituted e.g. by up to 4 substituents the same or different as hereinbefore described, especially lower alkyl, lower alkoxy, lower alkylthio, halogen, phenyl, halophenyl, lower alkylphenyl or lower alkoxyphenyl. Preferably m is 1. Preferably either or both $R^2$ and $R^3$ represent substituents selected from lower alkyl (e.g. methyl or ethyl) lower alkoxycarbonyl, (e.g. methoxycarbonyl); halogen (e.g. chlorine or bromine) or $R^2$ and $R^3$ are both hydrogen.

A preferred group of compounds for use in this invention has the general formula Id

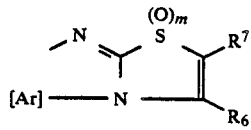

and salts thereof, wherein [Ar] represents

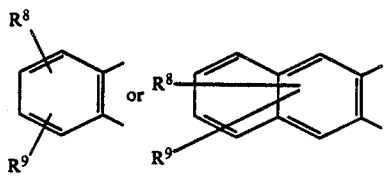

$R^7$ is a phenyl or a pyridyl group either of which may be substituted preferably by up to 3 substituents the same or different as hereinbefore defined, most preferably selected from lower alkyl, lower alkylthio, lower alkoxy and halogen; $R^8$ and $R^9$ independently represent hydrogen or a substituent selected from lower alkyl, lower alkoxy, halogen, cyano, carboxy, loweralkoxycarbonyl, alkanoyloxy of 2 to 7 carbon atoms, carbamoyl, hydroxy, hydroxyalkyl, haloloweralkyl, amino, carbamoyloxy, $R^6$ is as hereinbefore defined and m is 0 or 1.

The term "lower" as used herein to qualify a group means such a group contains 1 to 6 carbon atoms.

Preferred compounds of the invention include 2-(2-(5-ethylpyridyl)thiazolo[3,2-a]-benzimidazole, and 6- or 7-ethoxy-2-(2-pyridyl)thiazolo [3,2-a]-benzimidazole.

Examples of acid addition salts are those formed from inorganic and organic acids, in particular pharmaceutically acceptable acid addition salts such as the hydrochloride, hydrobromide, hydroiodide, sulphate, nitrate, phosphate, sulphonate (such as the methanesulphonate and p-toluenesulphonate)acetate, maleate, citrate, fumarate, tartrate, malonate and formate. The salts also include quaternary ammonium salts such as those formed from alkyl or aralkyl halides.

The compounds of formula I possess antiulcer and/or anti-secretory activity as measured by standard test procedures and accordingly are useful for the treatment of ulcers or hypersecretion in mammals.

Compounds of formula I were tested for antisecretory activity by their ability to inhibit the highly specific proton transporting enzyme $H^+/K^+$ ATPase.

Potential $H^+/K^+$ ATPase inhibitors were evaluated by a technique involving the measurement of aminopyrine accumulation in rabbit isolated gastric glands. Aminopyrine accumulates in acid-secreting cells; therefore, uptake of aminopyrine is increased by secretagogues and an inhibitor of acid secretion will reduce the response to one or more secretagogues depending upon its site of action. Compounds which reduce the response to dibutyryl cyclic adenosine monophosphate (DBcAMP) stimulation are assumed to have an intracellular site of action, and those which reduce the response to both DBcAMP and high potassium ion concentration ($K^+$) are thought to have an intracellular site of action at the secretory surface of the parietal cell, involving the highly specific proton - transporting enzyme, $H^+/K^+$ ATPase. The following test procedure is used:

Rabbit gastric glands are isolated from gastric mucosa from the corpus region of the stomach by a method based on one described by Berglindh T., Obrink K. J., Acta Physiol. Scand. 96, 150–159 (1976). Measurement of aminopyrine uptake is carried out using a procedure based on the method described by Berglindh T., Hellander H. F., Obrink K. J. (ibid.97, 401–414, 1976).

Compounds are tested at a concentration of $10^{-4}M$, initially, and in some cases at lower concentrations, for their ability to inhibit $^{14}C$-aminopyrine uptake in gastric glands, stimulated by DBcAMP and high $K^+$ respectively. Results are expressed as the % inhibition of the maximum response to the secretagogue induced by the test compound. An inhibitor of $H^+/K^+$ ATPase would be expected to reduce the response to both secretagogues.

In the above test the following compounds of formula I were particularly active giving the results shown:

| Compound | % Inhibition to stimulation by: | |
|---|---|---|
| | DBcAMP | $K^+$ |
| 2-(2-(5-ethylpyridyl)-thiazolo[3,2-a]benzimidazole | 56% at $10^{-4}$ M | 142% at $10^{-4}$ M |
| 6- or 7-ethoxy-2-(2-pyridyl)-thiazolo[3,2-a]-benzimidazole | 68% at $10^{-4}$ M | 162% at $10^{-4}$ M |
| 2-[2-(6-Phenylpyridyl)]-thiazolo[3,2-a]benzimidazole | 22% at $10^{-4}$ M | 381% at $10^{-4}$ M |

This invention also provides processes for preparing the novel compounds of formula I. In general the compounds may be prepared by processes which are known or are analogous to known processes—see literature references hereinbefore disclosed.

A first process for preparing compounds of formula I comprises cyclising a compound of formula

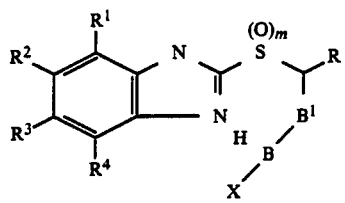

(II)

wherein —B—B$^1$—, n, m, R, R$^1$, R$^2$, R$^3$, R$^4$, R$^5$ and R$^6$ are as defined above, and X is OH or a leaving group such as halogen or an aryl-, alkyl- or aralkyl-sulphonyloxy group that couples B to nitrogen, providing that (i) when —B—B$^1$— has formula Ic and n is 1 then X is not OH; and (ii) when —B—B$^1$— has formula Ib then X is OH. This cyclisation is conveniently carried out in a suitable solvent if desired under basic conditions (e.g. triethylamine, potassium carbonate) and with heating if required. When X is enolic OH the cyclisation may be carried out in acidic solvent such as acetic anhydride.

Compound of formula II can in general be prepared by reacting an appropriate 2-chlorobenzimidazole with a compound of formula

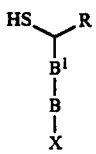

(III)

wherein R, —B—B$^1$— and X are as hereinbefore defined and if desired oxidising the product, e.g. using a peroxyorganic acid such as peroxybenzoic acids.

Compounds of formula II as hereinbefore defined wherein X is OH, —B—B$^1$— has the formula Ic wherein n is 0 (enol form of ketone) or formula Ib may be prepared by reacting the appropriate 2-mercaptobenzimidazole with a haloketone or aldehyde of formula IIIa or IIIb.

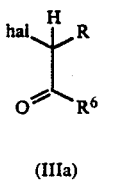 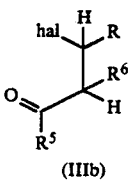

(IIIa)          (IIIb)

wherein R, R$^5$ and R$^6$ are as defined above and hal is a halogen.

By reacting an appropriate 2-mercaptobenzimidazole of formula

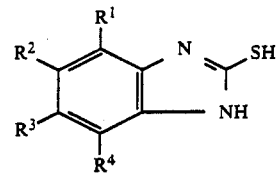

(IV)

wherein R$^1$, R$^2$, R$^3$ and R$^4$ are as defined above with a compound of formula

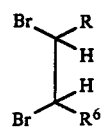

(V)

wherein R, R$^6$ and n are as hereinbefore defined, it is possible to isolate from such a reaction a corresponding compound of formula I wherein —B—B$^1$— is —(CHR$^5$)$_n$—CR$^6$= wherein n is 0. This reaction is conveniently carried out by heating in a suitable solvent, e.g. dimethylformamide, if desired in the presence of base.

It should be noted that due to tautomerism certain ring substituted 2-mercaptobenzimidazole starting materials are mixtures and hence mixtures of final products are obtained. For example 2-mercapto-5-methylbenzimidazole is tautomeric with 2-mercapto-6methylbenzimidazole and the final product will be a mixture of compounds where R$^2$ or R$^3$ is methyl.

A further process for preparing the compounds of formula I wherein m is 0 comprises cyclising a compound of formula

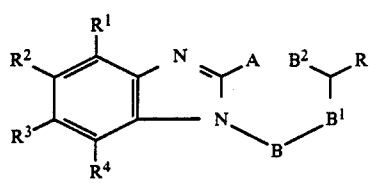

(VI)

wherein —B—B$^1$—, n, R, R$^1$, R$^2$, R$^3$, R$^4$, R$^5$ and R$^6$ are as hereinbefore defined and one of A and B$^2$ is —SH, the other is a leaving group providing that when A is SH then B$^2$ may also represent OH.

When A or B$^2$ is a leaving group the cyclisation is generally carried out by heating if desired in the presence of base, e.g. triethylamine, K$_2$CO$_3$, NaOH,etc. When B$^2$ is OH the cyclisation may be carried out in the presence of a strong acid, e.g. HCl or polyphosphoric acid.

Compounds of formula VI wherein A is SH and B$^2$ is OH may be prepared by (a) reacting an appropriate 2-chlorobenzimidazole with a compound of formula

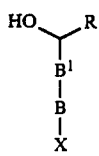

(VII)

wherein —B—B$^1$—, X, R, R$^5$ and R$^6$ are as hereinbefore defined to give a compound of formula VIII

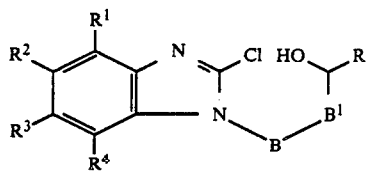
(VIII)

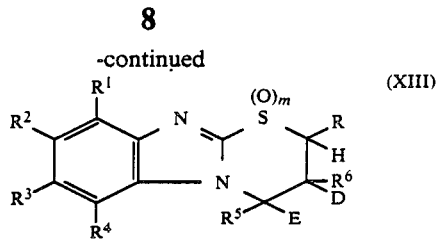
(XIII)

wherein —B—B$^1$—, R$^1$, R$^2$, R$^3$, R$^4$, R$^5$ and R$^6$ are as hereinbefore defined and (b) reacting the compound of formula VIII with thiourea and to give a 2-isothiouronium compound and treating this with an alkali metal hydroxide or ammonium hydroxide under mild conditions, e.g. reacting at room temperature or without heating.

Compounds of formula VIII wherein —B—B$^1$— is —(CHR$^5$)$_n$—CR$^6$= may be reacted in step (b) above under more vigorous conditions, e.g. reflux in a solvent such as a solvent with a boiling point above 50° C., to give a corresponding compound of formula I directly.

Compounds of formula VI wherein A is SH and B$^2$ is a leaving group and —B—B$^1$— has formula Ib may be prepared from the corresponding compounds of formula VI wherein B$^2$ is OH by known methods e.g. halogenation, sulphonylation to convert OH to a leaving group.

Compounds of formula VI wherein A is a leaving group such as halogen and B$^2$ is SH may be prepared by building up the molecule from appropriate starting materials wherein the —SH is protected by a thiol protecting group and removing the protecting group as the final step.

In yet a further process the compounds of formula I wherein m is 0 may be prepared by reacting a compound of formula

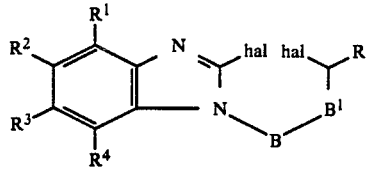
(XI)

wherein —B—B$^1$—, hal, n, R, R$^1$, R$^2$, R$^3$, R$^4$, R$^5$ and R$^6$ are as hereinbefore defined with (i) an alkali metal sulphide or hydrosulphide, or
(ii) ammonium sulphide or polysulphide or
(iii) H$_2$S in the presence of a tertiary amine.

Compounds of formula I as hereinbefore defined wherein —B—B$^1$— is —CR$^5$=CR$^6$— or —(CHR$^5$)$_n$—CR$^6$= may be prepared by reacting a compound of formula XII or XIII

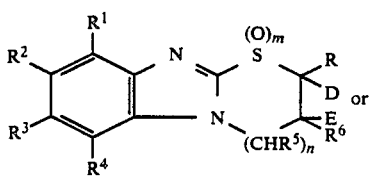
(XII)

in which formulae one of D and E is hydroxy or a leaving group such as hereinbefore defined, the other of D and E being hydrogen, to remove the elements of DE, e.g. dehydrohalogenation, dehydration, etc.

Yet a further process for preparing compounds of formula I wherein —B—B$^1$— is —(CHR$^5$)$_n$—CR$^6$= comprises cyclizing a compound of formula

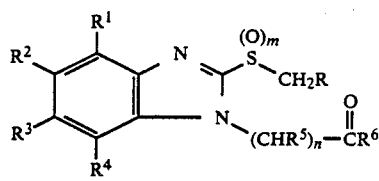
(XIV)

wherein R, R$^1$, R$^2$, R$^3$, R$^4$, R$^5$, R$^6$ and n are as hereinbefore defined. The cyclisation may be conveniently carried out under condensation conditions such as treatment with mixed base/acid systems, e.g. sodium formate/formic acetic anhydride or sodium acetate/acetic anhydride, or by treatment with base followed by subsequent dehydration under acid conditions.

Compounds of formula I wherein m is 0 and 1 may be interconverted. For example when m is 0 the compounds may be oxidised to the corresponding oxides of formula I wherein m is 1 by treatment with suitable oxidising agents e.g. hdyrogen peroxide, sodium periodate, peroxy acids such as peroxybenzoic acids and peroxyalkanoic acids. When m is 1 the compound of formula I may be reduced to the corresponding compound where m is 0 using a reducing agent such as a metal hydride. Accordingly compounds of formula I are intermediates for other compounds of formula I.

The compounds of formula I possess one or more asymmetric centres and hence optical isomers and mixtures thereof are possible. All such isomers and mixtures thereof are included within the scope of this invention. Where any reaction process produces mixtures of such isomers standard resolution techniques may be applied to separate a specific isomer.

In any of the aforementioned reactions compounds of formula I may be isolated in free base form or as acid addition salts as desired. Quaternary ammonium salts may be prepared by reaction with an appropriate halide.

Processes as described hereinabove which prepare novel compounds of formula I are within the scope of this invention.

For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carriers) is surrounded by carriers, which is thus in association with it. Similarly cachets are included.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10 to 75% of the glycol by weight is generally suitable. Other compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 10 to 500 mg or more, e.g. 25 mg to 250 mg, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients, e.g. aluminium hydroxide, magnesium hydroxide or bismuth carbonate, aluminium glycinate, calcium carbonate, magnesium trisilicate, sodium bicarbonate or the alumina gel described in British Specification No. 1,284,394.

In another aspect the invention provides as an anti-ulcer agent a compound of formula I or a pharmaceutically acceptable salt thereof as defined above.

The following Examples illustrate the invention:

EXAMPLE 1

6-Ethoxy-2-(2-pyridyl)thiazolo[3,2-a]-benzimidazole and 7-ethoxy-2-(2-pyridyl)thiazolo[3,2-a]benzimidazole 5-Ethoxy-2-mercaptobenzimidazole (10.43 g) was dissolved in 2-methyl-2-propanol (250 ml) at 30° C. Potassium tert-butoxide (5.95 g) was added and the mixture was left to stir for 1 hour. 2-(1,2-Dibromoethyl)pyridine hydrobromide (18.4 g) was added and the mixture was stirred at 30° C. for 1 hour and at reflux for 2 hours. The mixture was filtered and the filtrate was evaporated under reduced pressure. The residue was combined with the first solid obtained and was dissolved in 2NHCl. The aqueous solution was extracted with ethyl acetate, basified (NaCO$_3$) and extracted with dichloromethane. The organic layer was dried (MgSO$_4$) and the solvent removed under reduced pressure. The residue was purified by chromatography on Florisil using chloroform as eluent and then on silica using ethyl acetate as eluent. The solvent was removed to give a mixture of the title compounds (0.2 g) mp 150°–151° C.

Analysis: Found: C. 65.3; H, 4.1; N, 14.6; C$_{16}$H$_{13}$N$_3$OS requires: C, 65.1; H, 4.4; N, 14.2%.

EXAMPLE 2

2-(2-(5-Ethylpyridyl))thiazolo[3,2-a]-benzimidazole

5-Ethyl-2-vinylpyridine (12.0 g)(J.Amer.Chem.Soc., 68 1368 (1946)) was dissolved in dichloromethane (40 ml) and cooled to ice temperature with stirring. Then bromine (15.8 g) dissolved in dichloromethane (30 ml) was added dropwise over a period of 5 minutes and the reaction mixture stirred for further 10 minutes at ice temperature.

Anhydrous HBr gas was bubbled through the reaction solution in excess amount and solvent was removed under reduced pressure. The resulting residue was treated with propan-2-ol.

(10 ml) and the resulting yellow solid filtered, washed with ether and dried to yield 2-(1,2-dibromoethyl)-5-ethylpyridine hydrobromide (29.0 g) (86%).

2-Mercaptobenzimidazole (10.84 g) was suspended in 2-methylpropan-2-ol (170 ml) and potassium tert-butoxide (8.1 g) in 2-methylpropan-2-ol (70 ml) added and the reaction mixture stirred under nitrogen for 1 hour at 50° C. The reaction was then cooled to room temperature and 2-(1,2-dibromoethyl)-5-ethylpyridine hydrobromide (27.0 g) was added at once and the reaction mixture stirred at room temperature for 2 hours and then refluxed for 2 hours. Further potassium tert-butoxide (8.1 g) was added and the reaction mixture refluxed for 2.5 hours.

The solvent was removed under reduced pressure and the resulting residue treated with 2N HCl (200 ml) and water (100 ml) and the insoluble solid filtered off.

The resulting filtrate was washed with ethyl acetate and basified (2N NaOH) and extracted with dichloromethane. The dichloromethane extracts were dried (MgSO$_4$) and evaporated to dryness under reduced pressure. The resulting residue was purified by column chromatography, first, on alumina (grade III) using dichloromethane as the eluent and then on silica using EtOAc/hexane (85:15 v/v) as the eluent. The solvents were removed under reduced pressure from the fractions having an Rf value about 0.44 and the resulting residue treated with methyl acetate (2 ml). The resulting solid was removed by filtration, washed with small amount of hexane and dried to give title compound (0.4 g) m.p. 174°–175° C.

Analysis: Found: C, 68.7; H, 4.9; N, 14.7; C$_{16}$H$_{13}$N$_3$S requires C, 68.8; H, 4.7; N, 15.0%.

EXAMPLE 3

2-(2-Pyridyl)thiazolo[3,2-a]benzimidazole

A solution of 2-mercapto-1-[2-oxo-2-(2-pyridyl)ethyl]benzimidazole (1 g.) in polyphosphoric acid was heated at 140° C. for 1 hour. The solution was neutralised with Na$_2$CO$_3$ solution and extracted into EtOAc (700 ml). The extracts were dried (MgSO$_4$) and evaporated to give a solid which was recrystallised from EtOAc/EtOH to give the title compound (0.35 g.) mp 222°–4° C.

Analysis: Found: C, 67.3; H, 3.5; N, 16.4; $C_{14}H_9N_3S$ requires C, 66.9; H, 3.6; N, 16.7%.

EXAMPLE 4

2-[2-(6-Methylpyridyl)]thiazolo[3,2-a]benzimidazole

In a manner analogous to Example 3 1-[2-(6-Methyl-pyrid-2-yl)-2-oxoethyl-2-mercaptobenzimidazole (1.7 g) was reacted with polyphosphoric acid (20 g) to give the title compound as the ¼ hydrate, (0.8 g,), m.p. 235°–7° C.

Analysis: Found: C, 67.15; H, 4.1; N, 15.4%; $C_{15}H_{11}N_3S$. ¼$H_2O$ requires: C, 66.8;H,4.3;N, 15.6%.

EXAMPLE 5

2-[2-(6-Phenylpyridyl)]thiazolo[3,2-a]benzimidazole

In a manner analogous to Example 3 1-[2-(6-Phenyl-pyrid-2-yl)-2-oxoethyl]-2-mercaptobenzimidazole (2.0 g) is reacted with polyphosphoric acid to give the title compound (1.7 g) m.p. 267°–268° C.

Analysis: Found: C, 73.3; H, 4.0; N, 12.5%; $C_{20}H_{13}N_3S$ requires: C, 73.4; H, 4.0; N, 12.8%.

EXAMPLE 6

2-(2-Pyridyl)naphth[2',3':4,5]imidazo[2,1-b]thiazole

In a manner analogous to Example 3 1-(2-(2-pyridyl)-2-oxoethyl)-2-mercaptonaphtho[2,3-d]imidazole (1 g) was reacted with polyphosphoric acid to give the title compound (290 mg) mp 261.5° C. decomp.

Analysis: Found: C, 71.6; H, 3.6; N, 13.7; $C_{18}H_{11}N_3S$ requires C, 71.7; H, 3.7; N, 13.9%.

The starting materials used in Examples 3 to 6 may be prepared as illustrated below for the compound 2-mercapto-1-(2-(2-(4-methoxypyridyl))-2-oxoethyl)benzimidazole:

(a) 2-Bromoacetyl-4-methoxypyridine (11.5 g, 0.05) and 2-chlorobenzimidazole (7.5 g, 0.05 mole) were dissolved in dimethylformamide (75 ml) and cooled to 2° C. $K_2CO_3$ (12 g, 0.08 mole) was added and the temperature rose to 9° C. as the suspension was stirred for ½ hour. The mixture was added to $H_2O$ (200 ml) giving a solid which was removed by filtration. The mother liquors were extracted with ethyl acetate and the solid was dissolved in the extracts. The organic solution was washed (brine) and dried ($MgSO_4$) and purified by passage down a silica column and evaporated to dryness to give a sticky solid. Trituration with propan-2-ol/di-isopropyl ether gave 2-chloro-1-[2-(2-[4-methoxypyridyl])-2-oxoethyl]-benzimidazole (7.2 g).

(b) A mixture of the product of step (a) (7.2 g) and thiourea (2.4 g) in ethanol (50 ml) was stirred at ambient temperature for ½hour and heated at 60° C. for 2 hours. The solution was filtered and evaporated and the residue was dissolved in water and treated to excess with $NH_4OH$ to give a solid which was purified by chromatography on silica with ethyl acetate to give 2-mercapto-1-(2-(2-(4-methoxypyridyl))-2-oxoethyl)benzimidazole (2 g).

EXAMPLE 7

Using a procedure analogous to those hereinbefore described the following compounds of formula I are prepared:

(a) 6,7-dichloro-2-(2-(3,5-dimethylpyridyl))thiazolo[3,2-a]-benzimidazole;

(b) 6,7-dichloro-2-(2-(4-methoxypyridyl))thiazolo[,3,2-a]-benzimidazole;

(c) 6,7-dichloro-2-(2-(3,5-dichloropyridyl))thiazolo[3,2-a]benzimidazole;

(d) 6,7-dichloro-2-(2-pyridyl)thiazolo[3,2-a]benzimidazole;

(e) 2-(2-(4-methoxypyridyl)-6,7-dimethoxythiazolo[3,2-a]-benzimidazole;

(f) 2-(2-(3,5-dichloropyridyl)-6,7-dimethoxythiazolo[3,2-a]-benzimidazole;

2-(2-pyridyl)-6,7-dimethoxythiazolo[3,2-a]benzimidazole;

(h) 6,7-dimethyl-2-(2-(3,5-dimethylpyridyl))thiazolo[3,2-a]benzimidazole;

(i) 2-(2-(3,5-dichloropyridyl))-6,7-dimethylthiazolo[3,2-a]benzimidazole;

(j) 2-(2-pyridyl)-6,7-dimethylthiazolo[3,2-a]benzimidazole;

(k) 2-(2-(3,5-dimethylpyridyl))thiazolo[3,2-a]benzimidazole;

(l) 2-(2-(4-methoxypyridyl))thiazolo[3,2-a]benzimidazole;

(m) 2-(2-(3,5-dichloropyridyl))thiazolo[3,2-a]benzimidazole;

(n) 2-(2-(4-methylpyridyl))thiazolo[3,2-a]benzimidazole;

(o) 2-(2-(3-hydroxypyridyl))thiazolo[3,2-a]benzimidazole;

(p) 2-(2-(4-methoxy-3,5-dimethylpyridyl))thiazolo[3,2-a]benzimidazole;

(q) 2-(2-(3-methylpyridyl))thiazolo[3,2-a]benzimidazole;

(r) 2-(2-(4-phenylpyridyl))thiazolo[3,2-a]benzimidazole;

(s) 6- or 7-methoxy-2-(2-pyridyl)thiazolo-[3,2-a]benzimidazole;

(t) 6- or 7-trifluoromethyl-2-(2-pyridyl)-thiazolo[3,2-a]benzimidazole.

(u) 2-(2-(6-cyanopyridyl))thiazolo[3,2-a]benzimidazole.

EXAMPLE 8

2-(4-Ethylthio-3-methylpyrid-2-yl)thiazolo-[3,2-a]benzimidazole (a) 2-Chlorobenzimidazole is reacted with 2-bromoacetyl-4-ethylthio-3-methylpyridine in the presence of $K_2CO_3$ to give 2-chloro-1-[2-[4-ethylthio-3-methylpyridyl])-2-oxoethyl]benzimidazole. This is reacted with thiourea and treated with $NH_4OH$ to give 2-mercapto-1-(2-(2-(4-ethylthio-3-methylpyridyl))-2-oxoethyl)benzimidazole.

(b) A solution of 2-mercapto-1-(2-(2-(4-ethylthio-3-methylpyridyl))-2-oxoethyl)benzimidazole in polyphosphoric acid is heated at 140° C. for 1 hour. The solution is neutralised with $Na_2CO_3$ solution and extracted into EtOAc. The extracts are dried and evaporated and the residue purified by chromatography on silica to give the title compound.

EXAMPLE 9

2-(4-Ethylthio-3-methylpyrid-2-yl)thiazolo[3,2-a]benzimidazole-1-oxide

A solution of 2-(4-ethylthio-3-methylpyrid-2-yl)-thiazolo[3,2-a]benzimidazole (0.01 mole) is dissolved in $CH_2Cl_2$ solution (100 ml) at 0° C. and treated with m-chloroperoxybenzoic acid (0.01 mole) for 0.5 hours. The solution is then washed with sodium carbonate solution and dried ($MgSO_4$). Purification by chromatography on silica gives the title compound.

EXAMPLE 10

In a manner analogous to Example 8 the following compounds of formula (IA) are prepared according to the reaction scheme:

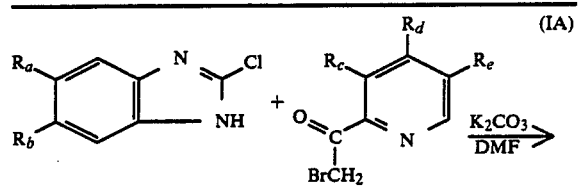

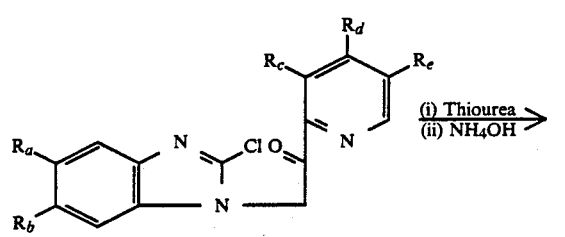

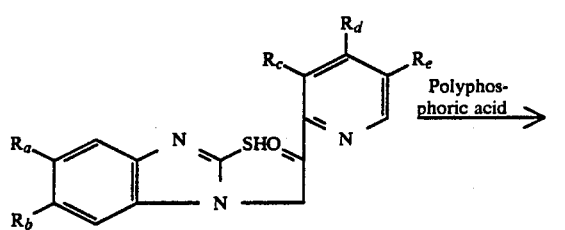

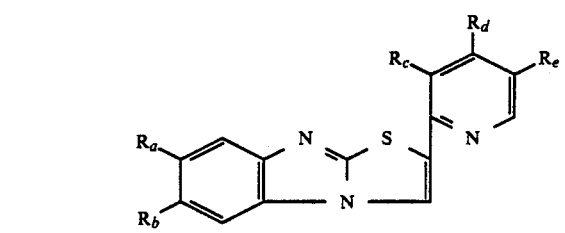

| $R_a$ | $R_b$ | $R_c$ | $R_d$ | $R_e$ |
|---|---|---|---|---|
| H | H | MeO | SEt | H |
| H | H | Me | SMe | H |
| H | H | Me | S$^n$Pr | H |
| OMe | H | Me | SEt | H |
| H | OMe | Me | SEt | H |
| H | H | Et | OPh | H |
| H | H | H | OCH$_2$Ph | H |
| H | H | Et | 4-morpholinyl | H |
| H | H | Et | 1-piperidinyl | H |
| CF$_3$ | H | Me | SEt | H |
| H | H | Me | SEt | Me |
| H | H | H | SPh | Me |
| H | H | Me | SCH=CH$_2$ | H |
| H | H | Me | SCH=CHCH$_3$ | H |
| H | H | Me | SC$_6$H$_{12}$ | H |
| H | H | H | SEt | OMe | which compounds are converted to the sulphoxides in a procedure analogous to Example 9.

We claim:

1. A method of treating ulcers or hypersecretion in a mammal which method comprises administering to said mammal in need of such treatment an antiulcer/antihypersecretion effective amount of a compound of formula

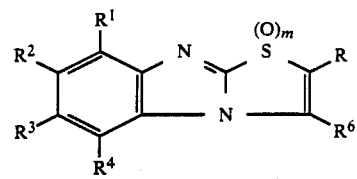

or a pharmaceutically acceptable salt thereof, wherein R represents a phenyl, naphthyl, pyridyl, thienyl, furyl, thiazolyl quinolyl, isoquinolyl or indolyl group, each optionally substituted by one or more substituents the same or different selected from lower alkylthio, lower alkyl, lower alkoxy, halogen, alkanoyloxy of 2 to 7 carbon atoms, lower alkoxycarbonyl, halolower alkyl, hydroxy, cyano, amino, mono- or diloweralkyl amino, lower alkanoylamino, carboxy, carboxylower alkyl, hydroxylower alkyl, carbamoyl, carbamoyloxy, lower alkyl-carbonyl, benzoyl, naphthoyl, (loweralkoxy) lower alkoxy, 1piperidinyl, 4-morpholinyl, 4-lower alkylpiperazinyl, 1-pyrrolidinyl, OR$^8$, SR$^8$, phenyl, and phenyl substituted by one or more substituents as hereinbefore defined excepting phenyl;

(where R$^8$ is C$_2$-C$_6$ alkenyl, C$_3$-C$_{10}$ cycloalkyl, phenyl, naphthyl, benzyl, or phenyl or naphthyl or benzyl or each carrying from 1 to 3 substituents on the aryl selected from lower alkyl, halogen, nitro, haloloweralkyl, hydroxy and lower alkoxy), R$^1$, R$^2$, R$^3$ and R$^4$ independently represent hydrogen, or a substituent as mentioned above in connection with the group R;

R$^6$ independently represents hydrogen or lower alkyl; and m is 0 or 1.

2. A pharmaceutical composition for treating ulcers or hypersecretion comprising an antiulcer/antihypersecretion effective amount of a compound of formula

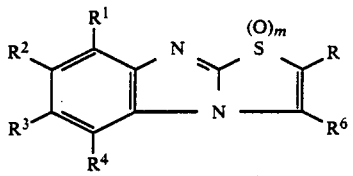

or a pharmaceutically acceptable salt thereof wherein R represents a phenyl, naphthyl, pyridyl, thienyl, furyl, thiazolyl, quinolyl, isoquinolyl or indolyl group, each optionally substituted by one or more substituents the same or different selected from lower alkylthio, lower alkyl, lower alkoxy, halogen, alkanoyloxy of 2 to 7 carbon atoms, lower alkoxycarbonyl, halolower alkyl, hydroxy, cyano, amino, mono- or diloweralkyl amino, lower alkanoylamino, carboxy, carboxyloweralkyl, hydroxylower alkyl, carbamoyl, carbamoyloxy, lower alkyl-carbonyl, benzoyl, naphthoyl, (loweralkoxy) lower alkoxy, 1-piperidinyl, 4-morpholinyl, 4-loweralkylpiperazinyl, 1-pyrrolidinyl, OR$^8$, SR$^8$, phenyl and phenyl substituted by one or more substituents as hereinbefore defined excepting phenyl;

(where R$^8$ is C$_2$-C$_6$ alkenyl, C$_3$-C$_{10}$ cycloalkyl, phenyl, naphthyl, benzyl, or phenyl or naphthyl or benzyl or each carrying from 1 to 3 substituents on the aryl selected from lower alkyl, halogen, nitro, haloloweralkyl, hydroxy and lower alkoxy), $R^1$, $R^2$, $R^3$ and $R^4$ independently represent hydrogen, or a substituent as mentioned above in connection with the group R;

$R^6$ independently represents hydrogen or lower alkyl; and m is 0 or 1, and a pharmaceutically acceptable carrier.

3. A compound of formula

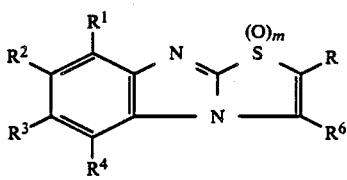

or a pharmaceutically acceptable salt thereof wherein
R represents a phenyl, naphthyl, pyridyl, thienyl, furyl, thiazolyl, quinolyl, isoquinolyl or indolyl group, each optionally substituted by one or more substituents the same or different selected from lower alkylthio, lower alkyl, lower alkoxy, halogen, alkanoyloxy of 2 to 7 carbon atoms, lower alkoxy carbonyl, halolower alkyl, hydroxy, cyano, amino, mono- or diloweralkyl amino, lower alkanoylamino, carboxy, carboxyloweralkyl, hydroxylower alkyl, carbamoyl, carbamoyloxy, lower alkylcarbonyl, benzoyl, naphthyl, (loweralkoxy) lower alkoxy, 1-piperidinyl, 4-morpholinyl, 4-loweralkylpiperazinyl, 1-pyrrolidinyl, $OR^8$, $SR^8$, phenyl and phenyl substituted by one or more substituents as hereinbefore defined excepting phenyl;

(where $R^8$ is $C_2$–$C_6$ alkenyl, $C_3$–$C_{10}$ cycloalkyl, phenyl, naphthyl, benzyl or pheneyl or naphthyl or benzyl or each carring from 1 to 3 substituents on the aryl selected from lower alkyl, halogen, nitro, haloloweralkyl, hydroxy and lower alkoxy), $R^1$, $R^2$, $R^3$ and $R^4$ independently represent hydrogen, or a substituent as mentioned above in connection with the group R;

$R^6$ independently represents hydrogen or lower alkyl; and m is 0 or 1, with the proviso that when $R^1$, $R^2$ and $R^4$ are hydrogen, $R^3$ is hydrogen or hydroxy and R is phenyl, p-chlorophenyl, p-bromophenyl, p-tolyl, p-methoxyphenyl, p-phenylphenyl, 1-naphthyl or 2-thienyl, then m is 1.

4. A compound as claimed in claim 3 wherein R represents phenyl, pyrid-2-yl or pyrid-3-yl each optionally substituted by one to three groups independently selected from lower alkyl, lower alkoxy, halogen, phenyl, halophenyl, lower alkylphenyl, lower alkoxyphenyl and lower alkylthio.

5. A compound as claimed in claim 3 wherein $R^2$ and $R^3$ are selected from hydrogen, lower alkyl, alkoxycarbonyl of 2 to 7 carbon atoms, halogen or lower alkoxy.

6. A compound as claimed in claim 3 which is 2-(2-(5-ethylpyridyl))thiazolo[3,2-a]benzimidazole or a pharmaceutically acceptable salt thereof.

7. A compound as claimed in claim 3 which is 6-ethoxy-2-(2-pyridyl)thiazolo[3,2-a]benzimidazole or a pharmaceutically acceptable salt thereof.

8. A compound as claimed in claim 3 which is 7-ethoxy-2-(2-pyridyl)thiazolo[3,2-a]benzimidazole or a pharmaceutically acceptable salt thereof.

* * * * *